US010561832B2

(12) United States Patent
Allard

(10) Patent No.: US 10,561,832 B2
(45) Date of Patent: *Feb. 18, 2020

(54) MEDICAL STOPCOCK, KIT COMPRISING SUCH A STOPCOCK, AND METHOD FOR PREPARING A MIXTURE OR AN EMULSION

(71) Applicant: Guerbet, Villepinte (FR)

(72) Inventor: Ludovic Allard, Millery (FR)

(73) Assignee: GUERBET, Villepinte (FR)

( * ) Notice: Subject to any disclaimer, the term of this patent is extended or adjusted under 35 U.S.C. 154(b) by 146 days.

This patent is subject to a terminal disclaimer.

(21) Appl. No.: 15/566,089

(22) PCT Filed: Apr. 15, 2016

(86) PCT No.: PCT/EP2016/058441
§ 371 (c)(1),
(2) Date: Oct. 12, 2017

(87) PCT Pub. No.: WO2016/166339
PCT Pub. Date: Oct. 20, 2016

(65) Prior Publication Data
US 2018/0093089 A1 Apr. 5, 2018

(30) Foreign Application Priority Data
Apr. 15, 2015 (FR) ..................... 15 53326

(51) Int. Cl.
*A61M 39/22* (2006.01)
*A61M 39/10* (2006.01)

(52) U.S. Cl.
CPC .......... *A61M 39/223* (2013.01); *A61M 39/10* (2013.01); *A61M 2039/1083* (2013.01);
(Continued)

(58) Field of Classification Search
CPC .... A61M 39/10; A61M 5/284; A61M 5/3134; A61M 5/31513; A61M 5/3129;
(Continued)

(56) References Cited

U.S. PATENT DOCUMENTS 3,161,195 A * 12/1964 Taylor ................... A61M 5/284
137/853
3,957,082 A * 5/1976 Fuson ................. A61M 5/1408
137/625.41
(Continued)

FOREIGN PATENT DOCUMENTS

BE 873375 A1 7/1979
DE 202013103615 U1 9/2013
(Continued)

OTHER PUBLICATIONS

Idée et al., "Use of Lipiodol as a Drug-Delivery System for Transcatheter Arterial chemoembolization of Hepatocellular Carcinoma: A Review", Critical Reviews in Oncology/Hematology, 2013, pp. 530-549, vol. 88.
(Continued)

*Primary Examiner* — Manuel A Mendez
(74) *Attorney, Agent, or Firm* — Thompson Coburn LLP; Steven M. Ritchey

(57) ABSTRACT

A medical stopcock comprising a body provided with three female connectors and a male connector, at least one of the female connectors being designed to receive an injection syringe; and a mobile plug which is mounted in the body, is provided with a rotation lever and comprises a fluid circulation channel; wherein the female connector designed to receive an injection syringe comprises a fool proofing device in order to prevent a mixing syringe from being mounted on this connector.

16 Claims, 4 Drawing Sheets

(52) U.S. Cl.
 CPC ............... *A61M 2039/1094* (2013.01); *A61M 2039/229* (2013.01)

(58) Field of Classification Search
 CPC .... A61M 39/26; A61M 39/045; A61M 39/22; A61M 5/007; A61M 5/28; A61M 5/14546; A61M 5/2448; A61J 1/20; A61J 1/2093; A61B 17/00491; A61B 17/8822
 See application file for complete search history.

(56) References Cited

U.S. PATENT DOCUMENTS

| | | | | |
|---|---|---|---|---|
| 4,807,666 | A | * | 2/1989 | Morse .................. F16K 5/0492 137/625.47 |
| 5,868,250 | A | * | 2/1999 | Brackett ............... A61M 5/008 206/363 |
| 6,349,850 | B1 | | 2/2002 | Cheikh |
| 7,306,768 | B2 | * | 12/2007 | Chiga ................... A61M 5/165 210/232 |
| 7,785,312 | B2 | * | 8/2010 | Thorne, Jr. ........... A61J 1/2096 604/500 |
| 8,308,340 | B2 | * | 11/2012 | Ferrante ........... A61B 17/00491 222/137 |
| 2009/0299270 | A1 | | 12/2009 | Buisson |
| 2012/0245564 | A1 | | 9/2012 | Tekeste et al. |
| 2013/0030348 | A1 | | 1/2013 | Lauer |
| 2014/0008366 | A1 | * | 1/2014 | Genosar ............... A61M 5/1782 220/265 |
| 2014/0276215 | A1 | | 9/2014 | Nelson et al. |

FOREIGN PATENT DOCUMENTS

| | | |
|---|---|---|
| EP | 1839699 A1 | 10/2007 |
| FR | 2804609 A1 | 8/2001 |
| RU | 2201743 C2 | 4/2003 |
| WO | 2012/024370 A1 | 2/2012 |
| WO | 2014/090958 A1 | 6/2014 |

OTHER PUBLICATIONS

International Search Report for PCT/EP2016/058441 dated Sep. 19, 2016.

Nakamura et al., "Transcatheter Oily Chemoembolization of Hepatocellular Carcinoma", Radiology, Mar. 1989, pp. 783-786, vol. 170, No. 3.

Written Opinion for PCT/EP2016/058441 dated Sep. 19, 2016.

* cited by examiner

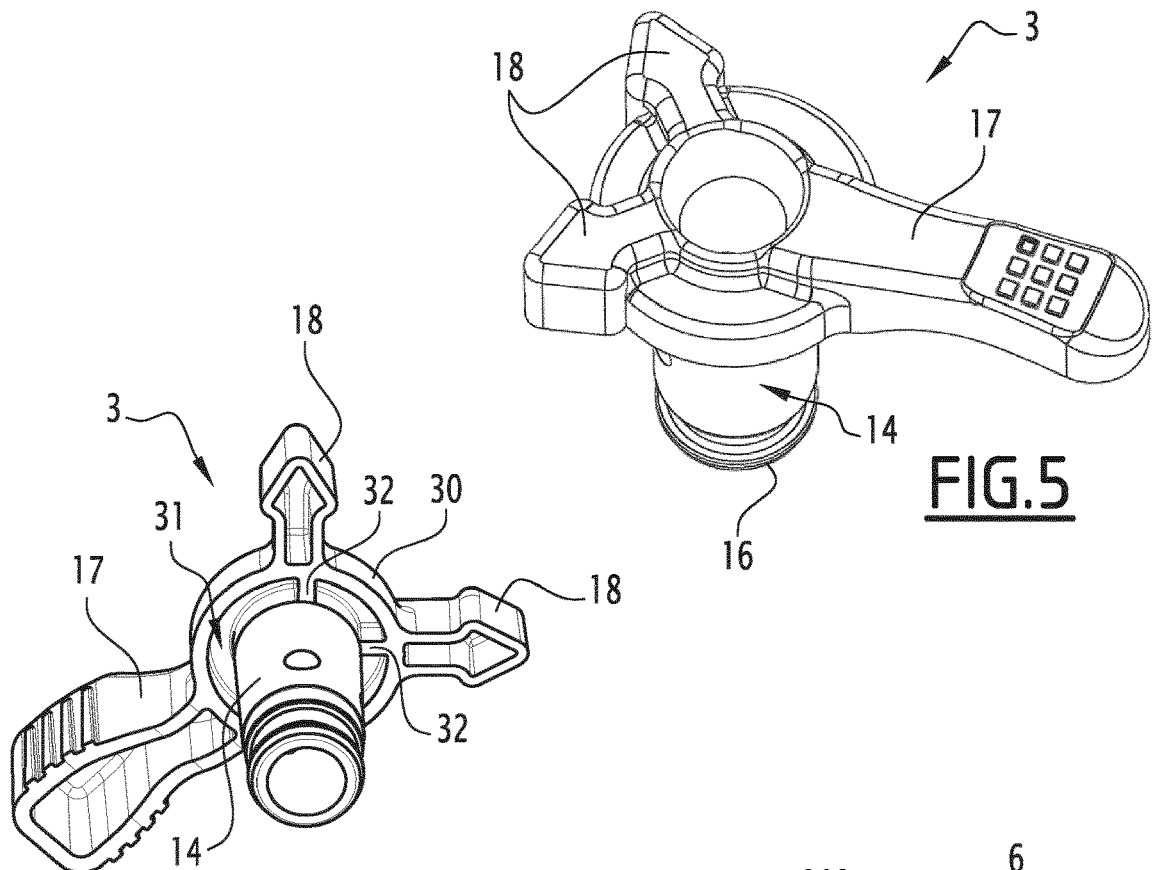
FIG.5
FIG.6
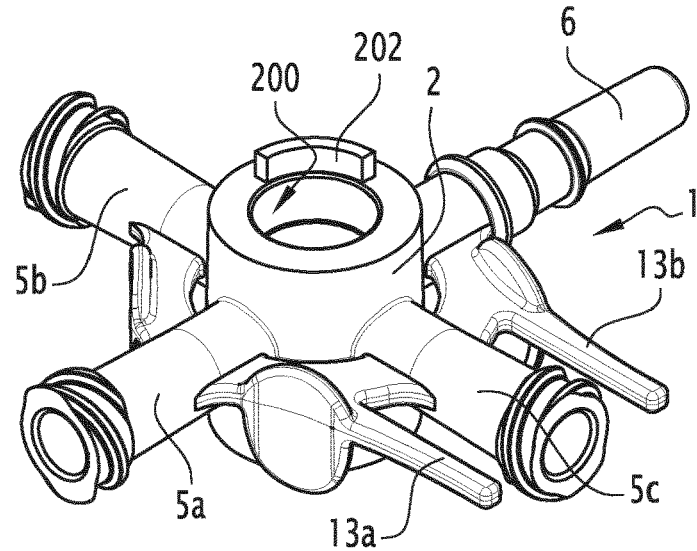
FIG.7
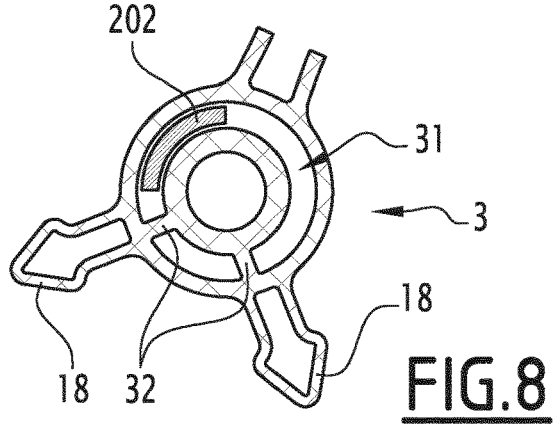
FIG.8

MEDICAL STOPCOCK, KIT COMPRISING SUCH A STOPCOCK, AND METHOD FOR PREPARING A MIXTURE OR AN EMULSION

CROSS-REFERENCE TO RELATED APPLICATIONS

This application is a U.S. National Phase application of PCT/EP2016/058441, filed on Apr. 15, 2016, claiming the benefit of French Application No. 1553326, filed on Apr. 15, 2015, both of which are incorporated herein by reference in their entireties.

The invention relates to a medical stopcock, to a kit for preparing a product to be injected, preferably a mixture or an emulsion, said kit comprising such a medical stopcock, and to a method for preparing a product or an emulsion intended to be injected into a patient, said method being carried out with the aid of such a preparation kit.

Iodinated oils have been used now for almost thirty years in interventional radiology procedures. Lipiodol® is characterized by its propensity to be captured selectively by hepatic tumors. This oil is therefore used as an anticancer agent vector for the treatment of hepatocellular carcinoma in a technique referred to as TransArterial ChemoEmbolization (TACE) (Nakamura et al.: Radiology, 1989; 170:783-6 and J. M. Idée—B. Guiu: Critical Reviews in Oncology/Hematology, 2013; 88 (3):530-49). The iodinated oils, in particular Lipiodol®, are also known to induce a transient embolization of the arterial circulation, thereby causing the latter to slow down. Given that most anticancer agents are soluble in water, the "emulsion" form, which is designed for mixing two phases that are non-soluble in each other, appears to be the most judicious for mixing an iodinated oil and an anticancer agent. It appears to be the most suitable for transporting, and delivering to a tumor, an anticancer agent that is too toxic and not sufficiently effective when administered in non-emulsified form by an intra-arterial route or systemic route.

To perform TACE, an interventional radiologist prepares the emulsion extemporaneously, just before the injection. He traditionally uses two 50-ml syringes connected to a stopcock which has three ports and which is provided with two female connectors, to which the syringes are connected, and a male connector, to which a catheter or a microcatheter can be fixed. One of the syringes contains a solution of an anticancer agent, while the other syringe contains an iodinated oil such as Lipiodol®. The emulsion is obtained, for example, after ten successive and rapid passages of the content of one syringe to the other, with the aid of a three-way stopcock. The emulsion is then transferred into one of the two mixing syringes, the empty mixing syringe is disconnected from the stopcock, and an injection syringe is then put in the place of the mixing syringe that has been removed. A small quantity of emulsion is transferred into the injection syringe by actuating the piston of the remaining mixing syringe. The injection is performed, over the course of ten minutes, into the right or left branch of the hepatic artery of a patient, irrigating the major part of the tumor.

Given that several successive injections are sometimes performed, the emulsion remaining in the mixing syringe is sometimes mixed again in the manner described above, after disconnection of the injection syringe and reconnection of the second mixing syringe. A new injection is performed after the transfer of the emulsion into one of the two mixing syringes, the disconnection of the empty mixing syringe from the stopcock, the connection of an injection syringe in place of the mixing syringe that has been removed, and the transfer of a small quantity of emulsion into the injection syringe by actuating the piston of the remaining mixing syringe.

The stopcocks made of plastic that are currently on the market and are intended for medical use, in particular intended for preparation of an emulsion that will be injected into a patient in the context of a transarterial chemoembolization technique, are for the most part stopcocks with three ports, and they pose different problems for the interventional radiologist performing this technique:

these stopcocks are rarely connected directly to a catheter or to a microcatheter. The injection syringe is in most cases disconnected from the stopcock then connected directly to one of these downstream devices.

these stopcocks involve disconnecting a mixing syringe and the injection syringe once or several times. This increases the risks of microbial contamination and of the practitioners coming into contact with the products contained in these syringes.

these stopcocks in most cases do not clearly indicate the path that is open.

these stopcocks do not have a device by which it is possible to avoid connecting a mixing syringe to the port intended for the injection syringe.

these stopcocks in most cases do not have a device facilitating its gripping and in particular the connection or disconnection of the syringes.

The patent FR 2 804 609 describes a four-port stopcock having connection means that can be reconfigured manually in order to permit the administration of a contrast medium via different tubes to a patient. Three ports of the stopcock have, at their end, a thread permitting the connection of a Luer cone, and the fourth port is designed for the connection of a catheter by way of a rotary connector. However, such a medical stopcock does not make it possible to avoid connecting a mixing syringe to the port intended for the injection syringe.

DE 20 2013 103 615 describes a medical stopcock having ports equipped with protruding elements by which it is possible to induce leaks when syringes equipped with incompatible connectors are joined, such that the practitioner notices the connection error. Such a solution does not make it possible to prevent errors of manipulation in a sufficiently reliable manner.

It is this disadvantage that the invention is intended to overcome by making available a novel medical stopcock by which it is possible to avoid connecting a mixing syringe to the port intended for the injection syringe, and the disadvantages that ensue from this.

To this end, the invention relates to a medical stopcock comprising a body provided with three female connectors and a male connector, at least one of the female connectors being designed to receive an injection syringe, and a mobile plug which is mounted in the body, provided with a rotation lever and comprising a fluid circulation channel. The female connector designed to receive an injection syringe comprises a foolproofing device making it possible to prevent the mounting of a mixing syringe on this connector.

By virtue of the invention, this medical stopcock makes it possible to obtain a mixture of injectable solution when syringes with different products are connected to it. This makes it possible to obtain a mixture or an emulsion of an aqueous solution, preferably of an anticancer agent and an iodinated oil, and to transfer this mixture or this emulsion into an injection syringe connected to a connector of this stopcock that will be specifically dedicated to it by virtue of the foolproofing device. The risks of errors of manipulation are thus reduced. It is considered that the invention relates to a medical assembly comprising a stopcock as mentioned above, at least one mixing syringe, and at least one injection syringe.

According to advantageous but non-obligatory aspects of the invention, such a medical stopcock can incorporate one or more of the following features, in any technically admissible combination:

- The foolproofing device is formed by two projections which are provided on each side of the female connector designed to receive an injection syringe and form insertion spaces with respect to this connector.
- The projections make it possible to prevent the mounting of syringes that are provided with a means prohibiting their connection to the female connector designed to receive an injection syringe.
- The fluid circulation channel brings only two connectors of the stopcock into fluidic communication.
- The fluid circulation channel is L-shaped.
- Two contiguous female connectors are designed for connection to mixing syringes.
- The medical stopcock comprises at least two gripping means designed for the placement of a finger.
- The plug comprises indicators by which it is possible to identify the connectors that are brought into fluidic communication by the positioning of the plug.
- The plug comprises, on the bottom of an upper part of this plug, a circular groove that is interrupted by ribs aligned with the indicators, while the body of the medical stopcock comprises, on its upper part, a means designed to slide in the circular groove and to be stopped by the ribs, preventing a rotation of the plug that would establish a communication between a female connector, designed for connection to a mixing syringe, and the male connector.
- The male connector comprises a movable locking ring which is clipped onto the distal end of said male connector.

The invention also relates to a preparation kit for preparing a product to be injected, said kit comprising a medical stopcock as mentioned above, two mixing syringes designed to be connected to a first and a second female connector of the stopcock, and an injection syringe designed to collect at least some of the product obtained by the mixing of the contents of the mixing syringes, effected by a reciprocating motion of the pistons of said mixing syringes, and designed to be connected to the female connector of the stopcock provided with a foolproofing device.

According to advantageous but non-obligatory aspects of the invention, such a preparation kit can incorporate one or more of the following features, in any technically admissible combination:

- The mixing syringes are syringes which, at their end, comprise fins that form means for prohibiting their connection to the connector comprising a foolproofing device.
- The injection syringe is a syringe which, at its distal end, comprises gripping beads which have a size smaller than the distance between the projections of the foolproofing device present on the connector.

The invention also relates to a method for preparing a mixture or an emulsion intended for injection into a patient, said method comprising steps of:

a) connecting two mixing syringes to two corresponding female connectors of a medical stopcock as mentioned above;

b) connecting an injection syringe to a female connector of the medical stopcock comprising a foolproofing device;

c) mixing an aqueous solution, contained in one of the mixing syringes, with an oil contained in the other mixing syringe after positioning a plug of the medical stopcock in such a way as to bring the mixing syringes into fluidic communication with each other, and effecting a reciprocating motion of the pistons of these mixing syringes until a mixture or an emulsion is obtained;

d) transferring some or all of the mixture or emulsion obtained in step c) into the injection syringe after positioning the plug in such a way as to bring one of the mixing syringes into communication with the injection syringe.

According to an advantageous but non-obligatory aspect of the invention, such a method can additionally comprise a supplementary step consisting in connecting a downstream device, preferably a catheter or a microcatheter, to a male connector of the medical stopcock, this step being either concomitant with step a), or subsequent to step b), or concomitant with step c), or subsequent to step d).

The invention will be better understood, and other advantages thereof will become more clearly apparent, in light of the following description of a medical stopcock, of a kit for preparing a product, preferably a mixture or an emulsion, and of a method for preparing a product, preferably a mixture or an emulsion, in accordance with its principle, said description being given by way of a non-limiting example and with reference to the attached drawings, in which:

FIG. 5 is a perspective view of the plug from FIG. 4, at a different angle;

FIG. 6 is a perspective view of another embodiment of a plug, at another angle;

FIG. 7 is a perspective view of the medical stopcock from FIG. 1, of which the plug is omitted;

FIG. 8 is a cross section of the medical stopcock from FIGS. 1 and 2, in a plane passing through the base of a lever of the plug;

Figure 1:
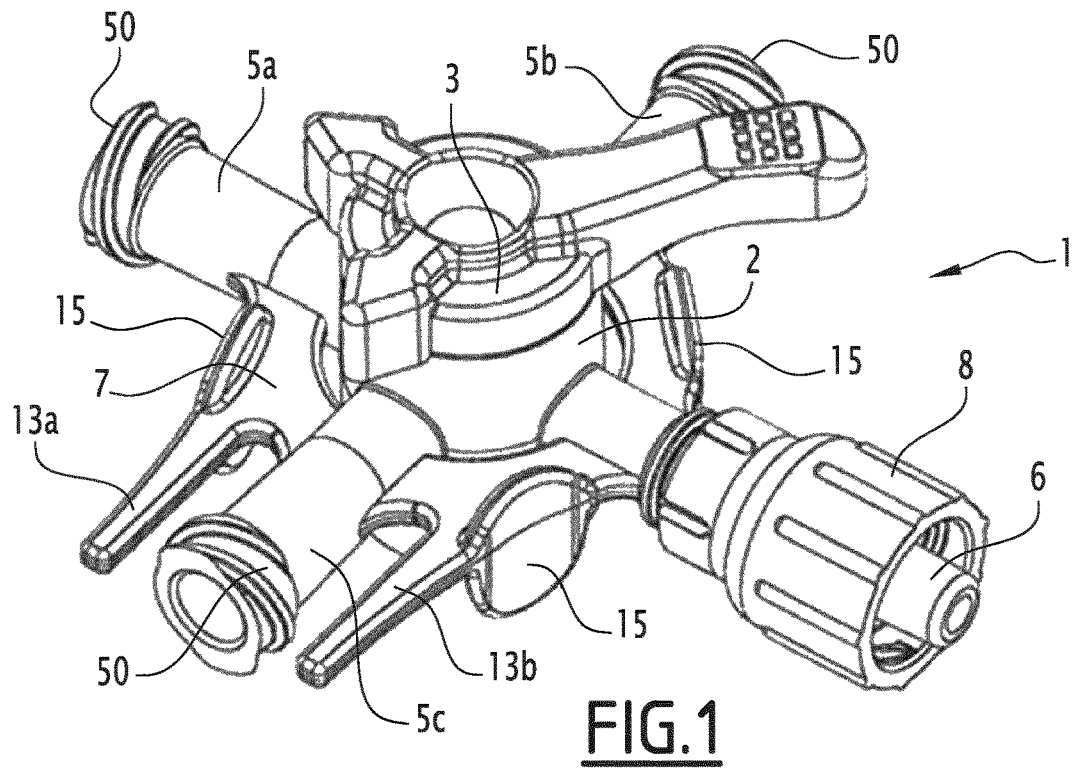
FIG. 1 is a perspective view of a medical stopcock according to the invention.
Figure 2:
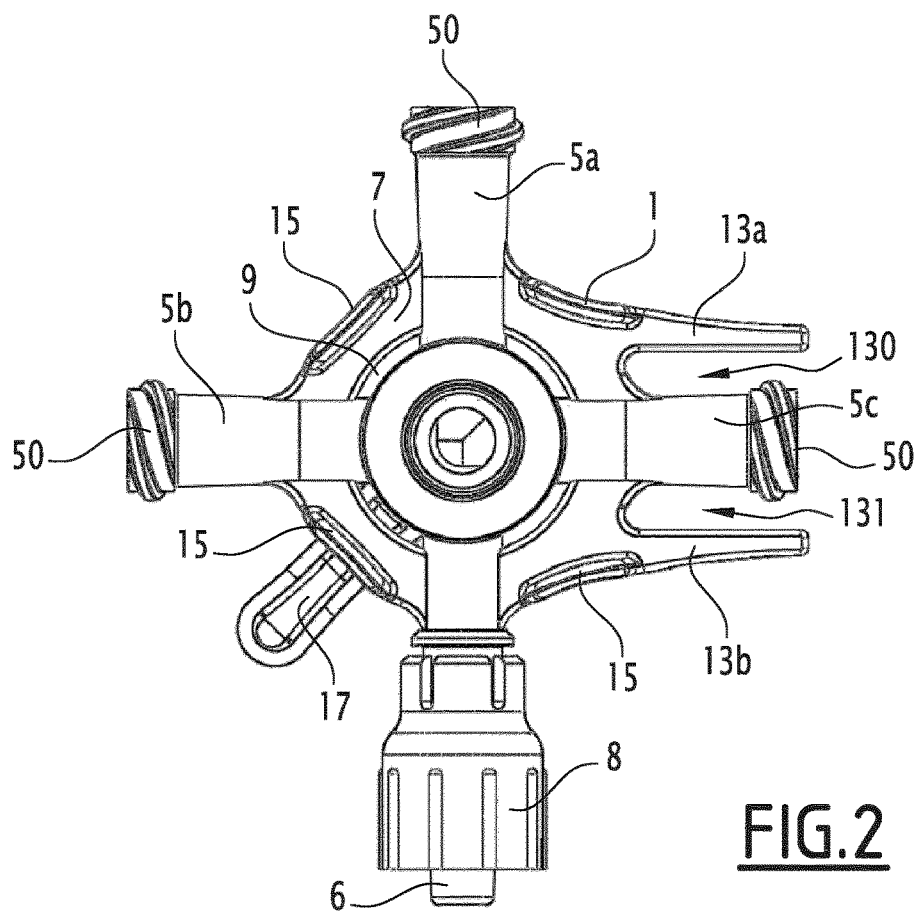
FIG. 2 is a plan view of the medical stopcock from FIG. 1.
Figure 3:
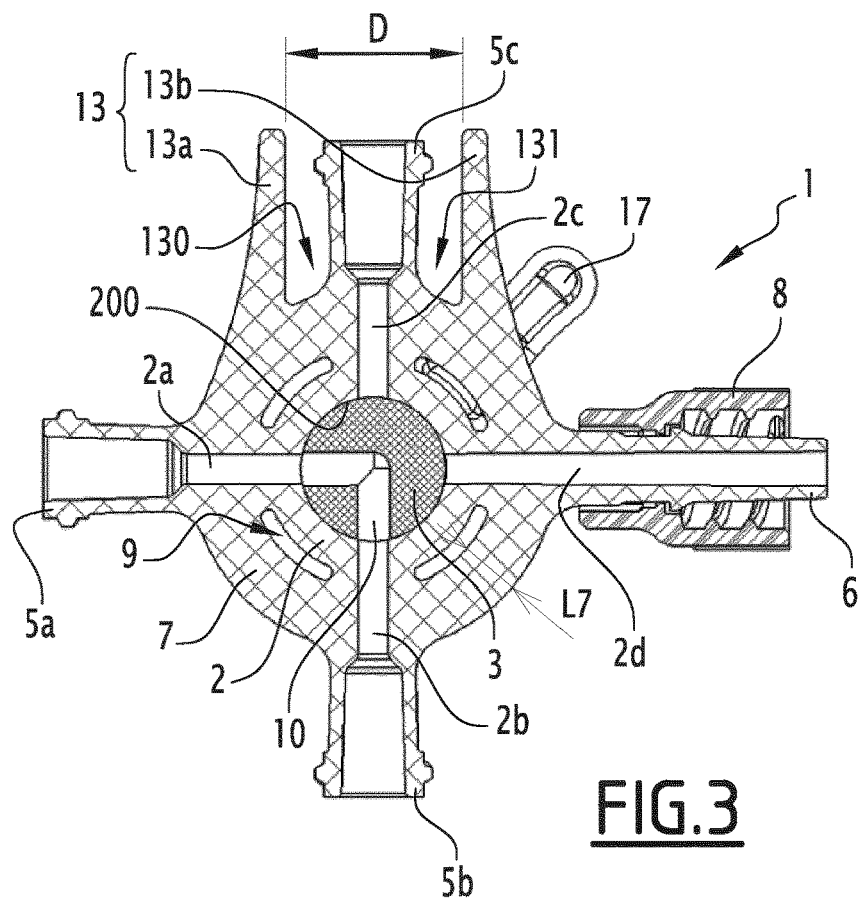
FIG. 3 is a cross section of the medical stopcock from FIGS. 1 and 2, in a plane comprising the central axes of four connectors of the medical stopcock.

FIGS. 1 to 3 show a medical stopcock 1 permitting the preparation of a mixture, preferably an emulsion, intended to be injected into a patient. The medical stopcock 1 comprises a hollow body 2 from which there extend three female connectors 5a, 5b and 5c and a male connector 6, preferably a Luer connector. The body 2 comprises a central bore 200, from which there extend four conduits 2a, 2b, 2c and 2d extending respectively through the connectors 5a, 5b, 5c and 6.

Figure 4:
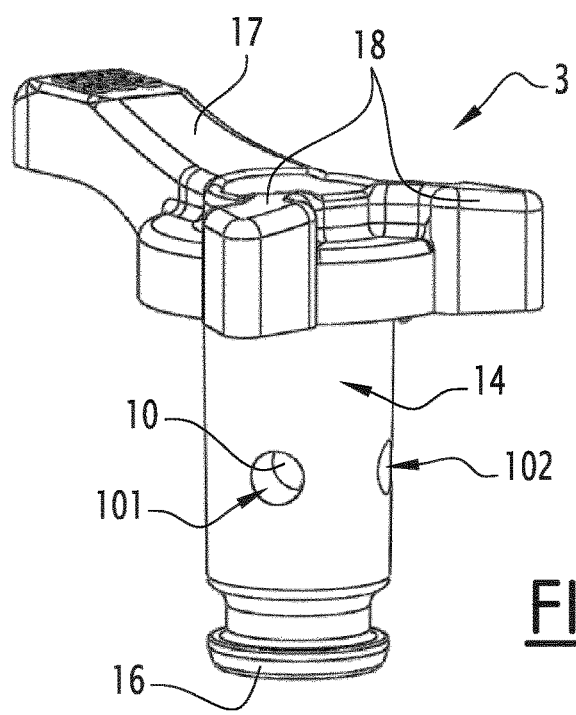
FIG. 4 is a perspective view of a plug of the medical stopcock from FIGS. 1 to 3.

The stopcock 1 comprises a plug 3, shown in particular in FIGS. 4 and 5, mounted rotatably in the bore 200. The plug 3 comprises a fluid circulation channel 10 for bringing the conduits 2a, 2b, 2c and 2d into communication in a manner described below. The plug 3 comprises an outer cylindrical wall 14 for ensuring the leaktightness of the stopcock 1 with the bore 200. An axial end of the plug 3 comprises a collar 16 with which it is held in the body 2 by clip fastening.

There are other solutions for holding the plug 3 in the body 2, for example snap riveting or the addition of a retention piece. Within the meaning of the present invention, "snap riveting" is understood as the creation of a mechanical bond between the plug 3 and the body 2, causing the partial deformation of the plug 3.

The plug 3 preferably comprises a lever 17 that can be actuated by a user, permitting the rotation of the plug 3 about its central axis.

According to the invention, one of the female connectors, the connector 5c in the example shown, comprises a foolproofing device 13. A "foolproofing device" is understood to mean a mechanical device by which it is possible to avoid assembling, mounting or connection errors by providing a visual indication and by defining a mechanical configuration that prevents the use of undesired elements. In the example shown, the foolproofing device 13 comprises two projections 13a and 13b which are provided on each side of the female connector 5c and which define two insertion spaces 130 and 131 that are situated between the projections 13a and 13b, respectively, and the connector 5c.

The foolproofing device 13 preferably prevents the connection of a syringe whose volume is greater than a predetermined value, by virtue of the geometry of the projections 13a and 13b and the width of the spaces 130 and 131, or of a syringe provided with a means prohibiting its connection to the connector 5c comprising this foolproofing device 13 and/or these projections 13a and 13b, on account of the incompatibility between this means and the mechanical configuration defined by the foolproofing device 13 and/or the projections 13a and 13b of this foolproofing device 13. Even more preferably, the foolproofing device 13 and advantageously the projections 13a and 13b of this foolproofing device 13 make it possible to prevent the mounting of syringes 20 and 21, preferably mixing syringes, provided with a means prohibiting their connection to the connector 5c comprising this foolproofing device 13 and/or the projections 13a and 13b of this foolproofing device. Preferably, when the projections 13a and 13b prevent the connection of a syringe provided with a means prohibiting its connection to the female connector 5c comprising this foolproofing device 13 and/or these projections 13a and 13b, on account of the incompatibility between this means and the mechanical configuration defined by the foolproofing device and/or the projections of this foolproofing device, they do not protrude more than 5 mm beyond the end of the female connector 5c. Preferably, when the projections 13a and 13b prevent the connection of a syringe whose reservoir has a diameter greater than a threshold value corresponding to a maximum volume, preferably of a mixing syringe, they protrude more than 5 mm beyond the end of the female connector.

Figure 9:
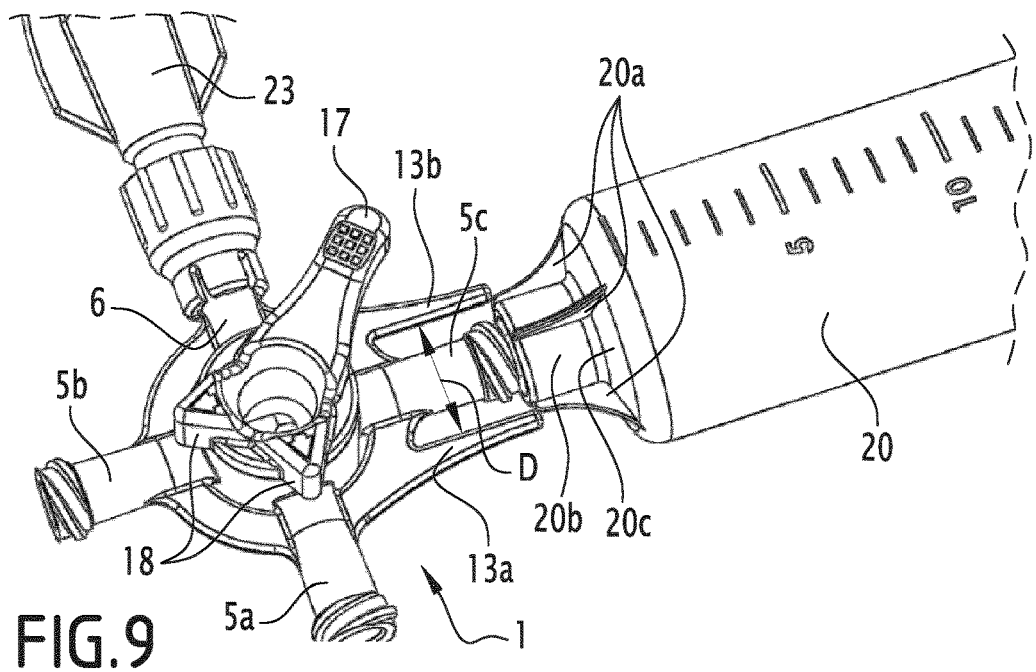
FIG. 9 is a perspective view of the medical stopcock from FIGS. 1 to 3, of a catheter connected to a connector of the medical stopcock, and a mixing syringe positioned in front of a female connector of the medical stopcock.
Figure 10:
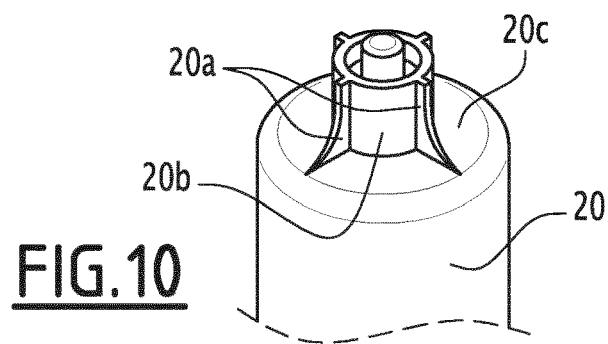
FIG. 10 is a perspective view of the end of a mixing syringe.

In the example shown in FIG. 9, the mixing syringe 20 is provided with means prohibiting its connection to the connector 5c comprising the foolproofing device 13. In this embodiment, the mixing syringe 20 comprises, at its end, fins 20a that form the means for prohibiting the connection of the mixing syringe 20 to the connector 5c comprising a foolproofing device. To screw a mixing syringe onto a female connector, preferably of the Luer type, it is necessary to effect between one and two turns of the syringe, depending on the Luer. Thus, the mixing syringe 20 comprises at least one fin 20a, preferably at least two fins 20a. This allows the foolproofing device 13 to perform its function. The end of the mixing syringe 20 is formed by a Luer connector comprising an inner male thread provided on a peripheral skirt 20b. The fins 20a are provided on the outer surface of the skirt 20b. As is shown in FIG. 9, the fins 20a create an obstruction at the end of the mixing syringe 20, around the skirt 20b of the male thread of the Luer connector, which obstruction is of a size greater than the distance D between the projections 13a and 13b. More preferably, the mixing syringe 20 comprises, at its end, four fins 20a positioned at 90° with respect to each other. This permits a better dimensional equilibrium of the body of the syringe and also permits better ergonomics in terms of gripping the syringe. The fins 20a of the mixing syringe 20 preferably have a shape for generating an interference with the projections 13a and 13b of the foolproofing device 13. Advantageously, these fins 20a make it easier to screw the mixing syringe 20 onto the connectors 5a or 5b, by improving the gripping of the syringe. Advantageously, the fins are contiguous to the outer skirt 20b of the male Luer lock thread and also to a conical end zone 20c of the reservoir of the syringe. These fins 20a preferably have an outer shape in the form of an arc of a circle. This allows the fingers to be placed on these fins and ensures good gripping of the mixing syringe 20 while remaining atraumatic.

The mixing syringe 21 is also provided with such a geometry.

The connectors 5a, 5b and 5c comprise a thread 50, to which a connection means permitting leaktight assembly of a medical device is connected. This connection means is preferably a Luer connector, which is the standard means of connection in the medical field and which is screwed onto the thread 50. This connection means attaches to the reservoir of the syringe. The projections 13a and 13b allow the insertion spaces 130 and 131 to be dimensioned in such a way that it is impossible to introduce therein syringes having a reservoir with a diameter greater than a threshold value corresponding to a maximum volume, or in such a way that it is impossible to connect a syringe on account of the incompatibility between at least one means present on said syringe and the mechanical configuration defined by the foolproofing device and/or its projections 13a and 13b.

The foolproofing device 13 preferably prevents the mounting, on the connector 5c, of syringes that have a means prohibiting their connection to the mechanical configuration defined by the foolproofing device, or syringes whose volume is greater than 3 ml. More preferably, the foolproofing device 13 makes it possible to prevent the mounting, on the connector 5c, of syringes having at least one means for prohibiting their connection to the mechanical configuration defined by the foolproofing device. The presence of fins at the end of the mixing syringes 20 and 21 prohibits their connection to the mechanical configuration defined by the foolproofing device, as is shown in FIG. 9. Thus, in this embodiment, it is not possible to connect a mixing syringe to the female connector 5c.

The risk of errors in manipulation, leading to the risk to patients, is greatly reduced since, by preventing connection to a mixing syringe, fluidic connection is impossible on account of the means which prohibit the connection and which are formed on the mixing syringe by the fins 20a. There is therefore no risk of an incorrect substance being injected into the patient since any transfer of fluid is impossible, as the mixing syringe is not able to be secured mechanically to the connector of the stopcock, in contrast to the system described in DE 20 2013 103 615.

Figure 11:
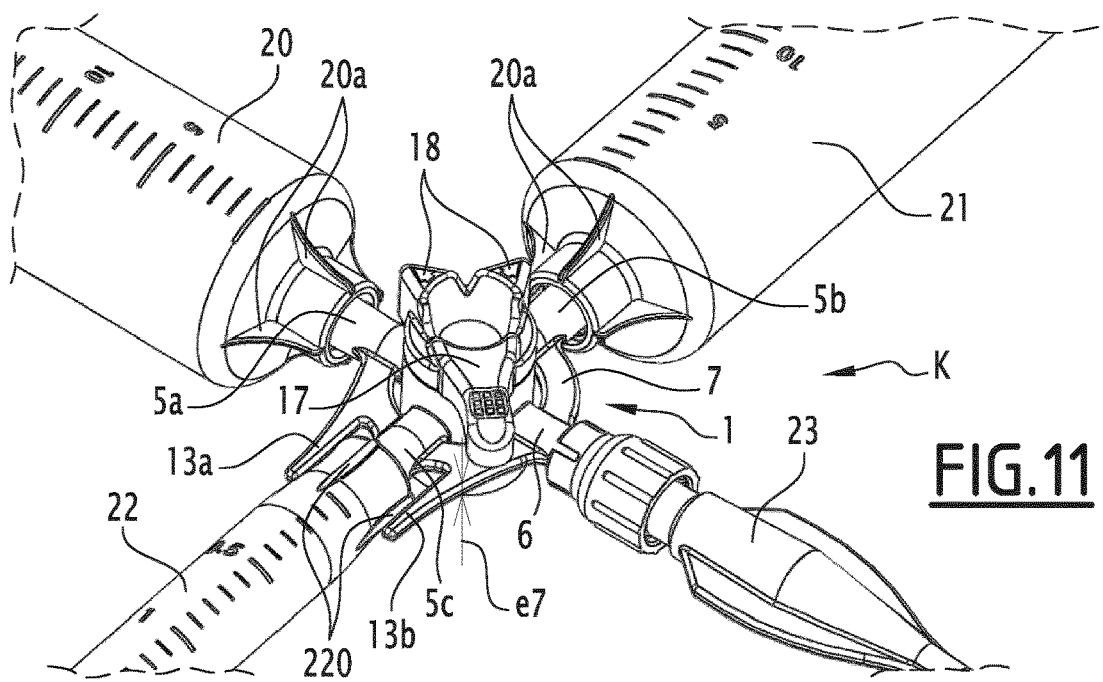
FIG. 11 is a perspective view of part of a preparation kit according to the invention.

The female connector 5c is preferably designed to be connected to an injection syringe 22, as is shown in FIG. 11. The external diameter of this syringe 22 and/or the size of the end of this syringe 22 allow it to be inserted into the insertion spaces 130 and 131 when it is screwed onto the connector 5c. At its distal end, the injection syringe 22 preferably comprises gripping beads 220 which have a size smaller than the distance D between the projections 13a and 13b.

In another embodiment, a syringe with a volume greater than 3 ml, like a mixing syringe 20, will not be able to be mounted on the connector 5c because its reservoir has too large a diameter.

The connectors 5a and 5b do not have a foolproofing device 13 and are therefore designed for the mounting of mixing syringes, as is shown in FIG. 11, in which two mixing syringes 20 and 21 are mounted on the connectors 5a and 5b.

An "injection syringe" is preferably understood as a syringe of small volume, that is to say a volume of between 1 ml and 3 ml. A "mixing syringe" is preferably understood as a syringe of large volume, that is to say a syringe with a volume greater than or equal to 10 ml.

Advantageously, the female connectors 5a and 5b are contiguous, which permits the connection of two contiguous mixing syringes.

Advantageously, the fluid circulation channel 10 brings only two of the connectors 5a, 5b, 5c and 6 of the stopcock 1 into communication. For this purpose, the fluid circulation channel 10 comprises only a single path provided with two openings 101 and 102 on the outer cylindrical wall 14. The use of the medical stopcock 1 is thus made safe. Indeed, only two paths are in communication regardless of the orientation of the plug 3, which makes it possible to perform three actions, but only one of these three actions at a time:
- mixing a first substance and a second substance contained, respectively, in the mixing syringes 20 and 21, which are connected to the connectors 5a and 5b, or
- transferring some of the mixture obtained and contained in one of the mixing syringes 20 and 21, into the injection syringe 22 connected to the connector 5c, or
- injecting into a patient, by way of a catheter connected to the connector 6, the mixture previously transferred into the injection syringe 22 connected to the connector 5c.

Thus, it will not be possible to inject the mixture into a patient while filling the injection syringe 22, or to mix the first and second substances contained in the mixing syringes 20 and 21, while transferring the mixture obtained into the injection syringe 22. The mixture is preferably an emulsion.

For this purpose, the fluid circulation channel 10 is L-shaped, which makes it possible to bring the mixing syringes 20 and 21 into fluidic communication, or to bring the mixing syringe 20 into fluidic communication with the injection syringe 22, or to bring the injection syringe 22 into fluidic communication with a downstream device such as a catheter 23 or a micro-catheter.

The plug 3 advantageously comprises visual indicators 18, such that the person using the stopcock 1 can tell, from the position of the plug 3, which connectors are in communication.

In the example shown, the indicators 18 are two arrows oriented at 90° to each other and showing the position of the fluid circulation channel 10.

Still more advantageously, as is shown in FIGS. 6 to 8, the plug 3, on the bottom of an upper part 30 carrying the lever 17 and the indicators 18, comprises a circular groove 31 that is interrupted by ribs 32 aligned with the visual indicators 18. On an upper part, the body 2 of the medical stopcock comprises a means preventing a rotation of the plug 3 that would establish a communication between the connector to which a mixing syringe is connected and the connector to which a downstream device is connected (that is to say would establish a communication between the connectors 5b and 6). This means is formed by a rib 202 which has a curved shape and which is designed to slide in the circular groove 31 between the ribs 32.

This stopcock 1 thus permits the preparation of a mixture or an emulsion of two substances that are contained in mixing syringes 20 and 21 or permits filling of an injection syringe 22 from one of the mixing syringes (preferably the syringe 20) or permits injection of the obtained mixture or emulsion into a patient. The device according to the invention is thus preferably a three-way stopcock with four ports.

The position of the ribs 32 is preferably linked to the position of the circular groove 31 on the plug 3. Thus, in another embodiment, the ribs 32 could be positioned differently, that is to say they could be non-aligned with respect to the visual indicators 18, on condition that their positioning makes it possible to prevent communication between the conduits 2b and 2d.

Advantageously, the medical stopcock 1 comprises at least two gripping zones that are designed for the placement of a finger. These gripping zones allow the stopcock 1 to be grasped more efficiently, thereby making it easier to manipulate during the steps of connection or disconnection of the syringes 20, 21 and 22, or during the orientation of the plug 3 to permit communication between one or other connector.

In the example shown, the stopcock 1 comprises four gripping zones 15, which are formed by flat circular shapes projecting from the body 2. These gripping zones 15 are distributed between the connectors 5a, 5b, 5c and 6.

Optionally, the medical stopcock 1 also comprises a reinforcement collar 7 rigidly connected to at least two of the connectors of the medical stopcock 1 and spaced apart from the central body 2 in order to form an openworked zone 9.

Advantageously, the reinforcement collar 7 is rigidly connected to three or four connectors of the medical stopcock 1. In the example shown, the reinforcement collar 7 is rigidly connected to the four connectors 5a, 5b, 5c and 6 and forms a complete belt around the body 2, thereby improving the stability of the stopcock 1.

It is important that the intersection between the reinforcement collar 7 and each connector is remote from the thread 50 of the connector, or more generally from the functional zone of the connector, which is most often the distal end of this connector, since the functional zone is the connection port on which or in which is inserted, for example, a syringe or the locking ring of a hose or of a catheter.

The reinforcement collar 7 is made of the same material as the body 2. In this case, the medical stopcock 1 is formed in one piece and from the same material.

Alternatively, the reinforcement collar 7 is made of a material different than that of the body 2 and of the plug 3. In such a case, the medical stopcock 1 is formed in one piece but involves an operation of overmolding the collar 7, which has the advantage of strengthening the mechanical stability of the latter. The overmolding of the reinforcement collar 7 is carried out using "filled" plastic materials. A "filled plastic material" is understood as a material in which a solid, non-miscible substance called a "filler" has been dispersed at the moment of injection. Preferably, the filler is chosen from among the compounds of the following list: mineral fillers in the form of powders such as synthetic silica, organic fillers such as wood flour or fruit peel or cellulose paste, fibrous reinforcing fillers such as glass fibers, and non-fibrous reinforcing fillers such as hollow glass microspheres or synthetic silica. The fibrous reinforcing fillers are able to improve the mechanical characteristics, the thermal stability and the dimensional stability of the material. Preferably, the reinforcement collar 7 is overmolded on the body 2 using a material filled with fibers such as glass fibers.

The reinforcement collar 7 has a width L7 greater than its thickness e7, which thus makes it possible to improve the moment of inertia and hence the mechanical strength of the stopcock 1. The reinforcement collar 7 preferably has a width L7 which is 3 to 10 times, preferably 3 to 7 times, more preferably 3 to 5 times greater than its thickness e7.

Preferably, the gripping means 15 are situated on the reinforcement collar 7.

In the example shown, the projections 13a and 13b of the foolproofing device 13 extend from the reinforcement collar 7. In an alternative not shown, it is possible that the projections 13a and 13b are not connected to the reinforcement collar 7 and extend, for example, from the connector 5c or from the body 2.

The body 2, the plug 3 and/or the reinforcement collar 7 forming the medical stopcock 1 are made from one or more materials that better withstand the mechanical and chemical stresses. Preferably, the body 2 and the reinforcement collar 7 are of a different material than the plug 3. The mechanical stresses are mainly the deformation by shearing and the pressure exerted on the stopcock 1 during its manufacture and/or its use. Moreover, the material from which the stopcock 1 is manufactured must be resistant to any pharmaceutical product, including oily products. Preferably, the material must be resistant to Lipiodol®. In addition or alternatively, the material of the body 2 and/or of the reinforcement collar 7 must be characterized by a high modulus of mechanical strength (Young's modulus). Thus, the medical stopcock 1, preferably its body 2 and its reinforcement collar 7, is made of the materials chosen from the following list: acrylonitrile butadiene styrene (ABS), copolymer of methyl methacrylate-acrylonitrile-butadiene styrene (MABS), polyester, polycarbonates (PC), alloys of polycarbonates, polysulfones, polyurethanes, polyether ketone ketone (PEKK), polyether ether ketone (PEEK), polyaryl ether ketones (PAEK), polymethyl methacrylate (PMMA), polyetherimides, polyamides (PA), preferably PA11 and PA12, polymethylpentene (TPX), polysulfone (PSU), cyclic olefin copolymers (COC), cyclic olefin polymers (COP), fluoroplastics other than polytetra-fluoroethylene (PTFE) and phosphoenolpyruvate (PEP) and combinations of these materials (for example ABS-PC). Preferably, the medical stopcock 1, more preferably its body 2 and its reinforcement collar 7, is made of the materials chosen from the following list: acrylonitrile butadiene styrene (ABS), copolymer of methyl methacrylate-acrylonitrile-butadiene styrene (MABS), polycarbonates (PC), polyether ether ketone (PEEK), polymethyl methacrylate (PMMA), polyamides (PA), preferably PA11 and PA12, polymethylpentene (TPX), polysulfone (PSU), cyclic olefin copolymers (COC), cyclic olefin polymers (COP). Still more preferably, the medical stopcock 1, more preferably its body 2 and its reinforcement collar 7, is made of the materials chosen from the following list: polyether ether ketone (PEEK), polymethyl methacrylate (PMMA), polyamides (PA), preferably PA11 and PA12, polymethylpentene (TPX) and polysulfone (PSU). Preferably, the medical stopcock 1 comprises polyamide or is composed of polyamide.

Preferably, the plug 3 of the stopcock is made of a softer material than the body 2 and/or than the reinforcement collar 7 of this stopcock. Thus, the plug 3 of the stopcock is preferably made of the materials chosen from the following list: polyethylene (PE), polypropylene (PP), polyoxymethylene (POM) or polybutylene terephthalate (PBT). This material must allow the plug 3 to be able to conform slightly within the body 2 of the stopcock. Moreover, the fact that the body 2 and the plug 3 are made of different materials makes it possible to improve the properties of rotation of the plug 3 in the body 2 of the stopcock. The plug 3 is more preferably made of POM.

Advantageously, the female connectors 5a, 5b and 5c are inlet ports, while the male connector 6 is an outlet port.

In one embodiment, the male connector 6 comprises a locking ring 8, which is fixed. This ring is therefore rigidly connected to the connector 6 and, more generally, to the body 2 of the stopcock 1.

Preferably, and in the example shown, the male connector 6 comprises a locking ring 8 which is clipped onto the distal end of the male connector 6. The locking ring 8 is then movable and makes it possible to strengthen the connection of the male connector 6 to a female connector of a downstream device (for example a catheter 23 or a microcatheter). More preferably, the locking ring 8 turns on the axis of the male connector 6, which for its part remains fixed. This has the advantage of making the connection manipulation easier and without any risk of disconnection.

As is shown in FIG. 11, the medical stopcock 1 permits formation of a preparation kit K for preparing a product to be injected, preferably a mixture or an emulsion, with two mixing syringes 20 and 21 and an injection syringe 22. The female connectors 5a and 5b are connected to a first mixing syringe 20 and to a second mixing syringe 21, respectively, and the female connector 5c comprising the foolproofing device 13 is connected to an injection syringe 22.

The preparation kit can also comprise a downstream device, such as a catheter 23 or a microcatheter permitting the injection, into a patient, of the product to be injected that is contained in the injection syringe 22. The catheter 23 is mounted and locked on the male connector 6 by virtue of the locking ring 8.

Preferably, it is the connector that comprises a foolproofing device 13, which is arranged on the path of communication with a downstream device, such as a catheter 23 or a microcatheter. Preferably, the foolproofing device 13 according to the present invention prevents the connection of at least one of the elements of the kit, still more preferably of at least two of the elements of the kit. Still more preferably, the foolproofing device 13 according to the present invention prevents the connection of the mixing syringes 20, 21.

Preferably, the kit elements whose connection is prevented by the foolproofing device 13 are provided with means prohibiting their connection to the connector 5c that comprises the foolproofing device 13. These means prohibiting the connection of elements of the kit to the connector 5c that comprises the foolproofing device 13 are preferably fins situated at the end of said elements of the kit.

The preparation kit can also comprise accessories for collecting the solutions, facilitating the filling of the mixing syringes 20 and 21.

The preparation kit K permits the implementation of a method for preparing a mixture or an emulsion intended to be injected into a patient. This method comprises the following steps. In a first step, two mixing syringes 20 and 21 are mounted on two corresponding female connectors 5a and 5b of the stopcock 1.

In a second step, which can be carried out at the same time as the first step, the injection syringe 22 is mounted on the female connector 5c of the stopcock 1, comprising the foolproofing device 13.

Preferably, the mixing syringes 20 and 21 respectively contain an aqueous solution and an oil, preferably an iodinated oil. Said aqueous solution comprises at least one anticancer agent and, optionally, at least one densifying agent.

Advantageously, the anticancer agent that the aqueous solution present in one of the two mixing syringes can comprise is chosen from among the anthracyclines and, more preferably, from among doxorubicin, epirubicin, nemorubicin and idarubicin. In an advantageous embodiment, the aqueous solution can thus additionally comprise a densifying agent, preferably at least one non-ionic iodinated contrast medium. The non-ionic iodinated medium, which can be used as such as a densifying agent, is preferably chosen from among iobitridol (Xenetix®), iopamidol (Iopamiron®, Isovue®), iomeprol (Iomeron®), ioversol (Optiray®, Optiject®), iohexol (Omnipaque®), iopentol (Imagopaque®), ioxitol (Oxilan®), iopromide (Ultravist®), metrizamide (Amipaque®), iosarcol (Melitrast®), iotrolan (Isovist®), iodixanol (Visipaque®), iosimenol and iosimide (Univist®), and a mixture of these. Iobitridol is the preferred non-ionic iodinated medium.

Advantageously, the iodinated oil that one of the mixing syringes can contain comprises or is composed of iodinated fatty acid derivatives, preferably iodinated fatty acid ethyl esters, more preferably iodinated fatty acid ethyl esters of poppy seed oil, of olive oil, of rapeseed oil, of peanut oil, of soybean oil or of walnut oil, still more preferably iodinated fatty acid ethyl esters of poppy seed oil or of olive oil. More preferably, this iodinated oil comprises or is composed of iodinated fatty acid ethyl esters of poppy seed oil, also called blue seeded opium poppy or *Papaver somniferum* var. *nigrum*.

A third step consists in mixing the aqueous solution contained in the mixing syringe 20 with the oil contained in the mixing syringe 21, after positioning the plug 3 in such a way as to bring the mixing syringes 20 and 21 into communication by way of the conduits 2a and 2b, and effecting a reciprocating motion of the pistons of the mixing syringes 20 and 21 until a mixture or an emulsion is obtained.

Thereafter, in a fourth step, some or all of the mixture or of the emulsion obtained in the mixing step is transferred into the injection syringe 22, after positioning the plug 3 in such a way that the mixing syringe 20, into which some or all of the mixture or of the emulsion obtained in the mixing step has been transferred, is brought into communication with the injection syringe 22 by way of the conduit 2a and the conduit 2c.

Preferably, the fourth step is carried out once the user of the stopcock determines visually that the mixture or the emulsion is homogeneous.

The catheter 23 is fitted simultaneously with the mixing syringes 20 and 21 and/or with the injection syringe 22, or after the mixing step has been carried out, or after the step of transferring some of the mixture or of the emulsion into the injection syringe 22. Preferably, the catheter 23 is mounted on the male connector 6 after this fourth transfer step has been carried out.

By positioning the plug 3 in such a way that the injection syringe 22 is in communication with the catheter 23, and by then actuating the piston of the injection syringe 22, the mixture or the emulsion can then be injected directly into a patient.

Once the mixing syringes 20 and 21, the injection syringe and the catheter 23 have been connected to the stopcock 1, an additional step of mixing the mixture or the emulsion obtained in the third step can be performed, in the case where the user determines visually that the mixture or the emulsion has undergone phase separation. This is an important advantage of the stopcock according to the invention over the other stopcocks of the prior art, which require disconnection of the mixing syringes or of the injection syringe, thus increasing the risks of air entering the injection device.

The mixing syringe 20 is brought into communication with the injection syringe 22, or the injection syringe 22 is brought into communication with the catheter 23, by suitably positioning the fluid circulation channel 10 of the plug 3 by a rotation movement of the lever 17. The correct positioning of the plug 3 for the preparation step to be carried out is verified with the aid of the arrow-shaped indicators 18. By way of example, in FIG. 11, the plug 3 is positioned in such a way as to bring the connectors 5a and 5b into fluidic communication, as indicated by the arrows 18, in order to permit mixing of the contents of the mixing syringes 20 and 21.

The foolproofing device 13 eliminates the risk of a mixing syringe 20 or 21 being connected to the connector 5c intended for the injection syringe 22 and prevents errors from being committed in the preparation of the mixture that is to be injected into the patient. By virtue of the foolproofing device 13, there is only one female connector on which the injection syringe 22 can be mounted, and the mixing syringes 20 and 21 can only be mounted on the remaining female connectors, which are positioned in a contiguous manner. This ensures the reliability of the medical stopcock 1.

The features of the embodiments and variants described above can be combined to form new embodiments of the invention.

The invention claimed is:

1. A medical stopcock comprising:
   a body provided with three female connectors and a male connector, at least one of the female connectors being designed to receive an injection syringe and at least one of the female connectors being designed to receive a mixing syringe; and
   a mobile plug, which is mounted in the body, is provided with a rotation lever and comprises a fluid circulation channel,
   wherein the female connector designed to receive an injection syringe comprises a fool proofing device in order to prevent the mixing syringe from being mounted on this connector.

2. The medical stopcock as claimed in claim 1, wherein the fool proofing device is formed by two projections which are provided on opposite sides of the female connector designed to receive an injection syringe, each of the projections defining an insertion space between the respective projection and to this female connector.

3. The medical stopcock as claimed in claim 2, wherein the projections make it possible to prevent the mounting of syringes that are provided with a means prohibiting their connection to the female connector designed to receive an injection syringe.

4. The medical stopcock as claimed in claim 1, wherein the fluid circulation channel comprises only a single path provided with two openings, the stopcock body and the openings being configured so that at most two connectors of the stopcock can be brought into fluidic communication by positioning the mobile plug.

5. The medical stopcock as claimed in claim 4, wherein the fluid circulation channel is L-shaped.

6. The medical stopcock as claimed in claim 1, wherein two contiguous female connectors are designed for connection to mixing syringes.

7. The medical stopcock as claimed in claim 1, wherein said stopcock comprises at least two gripping means designed for the placement of a finger.

8. The medical stopcock as claimed in claim 1, wherein the mobile plug comprises indicators by which it is possible to identify the connectors that are brought into fluidic communication by the positioning of the mobile plug.

9. The medical stopcock as claimed in claim 8, wherein the mobile plug comprises, on the bottom of an upper part of this plug, a circular groove that is interrupted by ribs aligned with the indicators, and in that the body of the medical stopcock comprises, on its upper part, a means designed to slide in the circular groove and to be stopped by the ribs, preventing a rotation of the mobile plug that would establish a communication between a female connector, designed for connection to a mixing syringe, and the male connector.

10. The medical stopcock as claimed in claim 1, wherein the male connector comprises a locking ring which is clipped onto the distal end of said male connector so as to be movable relative to the male connector.

11. A preparation kit for preparing a product to be injected, wherein said preparation kit comprises:
a medical stopcock as claimed in claim 1, wherein the mobile plug is rotatable by the rotation lever to a position that brings only the first and second female connectors into fluidic communication with each other,
two mixing syringes designed to be connected to a first and a second female connector of the stopcock and, when so connected and when only the first and second female connectors are in fluidic communication with each other, to effect mixing of their respective contents by a reciprocating motion of their respective pistons; and
an injection syringe designed to collect at least some of the product obtained by the mixing of the contents of the mixing syringes, and designed to be connected to the female connector of the stopcock that is provided with the fool proofing device.

12. The preparation kit as claimed in claim 11, wherein each of the mixing syringes is a syringe which comprises at least one fin at its end as a means prohibiting its connection to the connector comprising a fool proofing device.

13. The preparation kit as claimed in claim 11, wherein the injection syringe is a syringe which, at its distal end, comprises gripping beads which have a size smaller than the distance between the projections of the fool proofing device present on the connector.

14. A method for preparing a mixture or an emulsion intended for injection into a patient, wherein the method comprises steps of:
a) connecting two mixing syringes to two corresponding female connectors of a medical stopcock as claimed in claim 1;
b) connecting an injection syringe to a female connector of the medical stopcock comprising a fool proofing device;
c) mixing an aqueous solution, contained in one of the mixing syringes, with an oil contained in the other mixing syringe after positioning a mobile plug of the medical stopcock in such a way as to bring the mixing syringes into fluidic communication with each other, and effecting a reciprocating motion of the pistons of these mixing syringes until an emulsion is obtained; and
d) transferring some or all of the mixture or emulsion obtained in step c) into the injection syringe after positioning the mobile plug in such a way as to bring one of the mixing syringes into communication with the injection syringe.

15. The preparation method as claimed in claim 14, where the method additionally comprises a supplementary step consisting in connecting a downstream device to a male connector of the medical stopcock, this supplementary step being either concomitant with step a), or subsequent to step b), or concomitant with step c), or subsequent to step d).

16. The medical stopcock as claimed in claim 1, wherein the male connector comprises a locking ring which is mounted onto the distal end of said male connector so as to be movable relative to the male connector.

* * * * *